Figure 1:
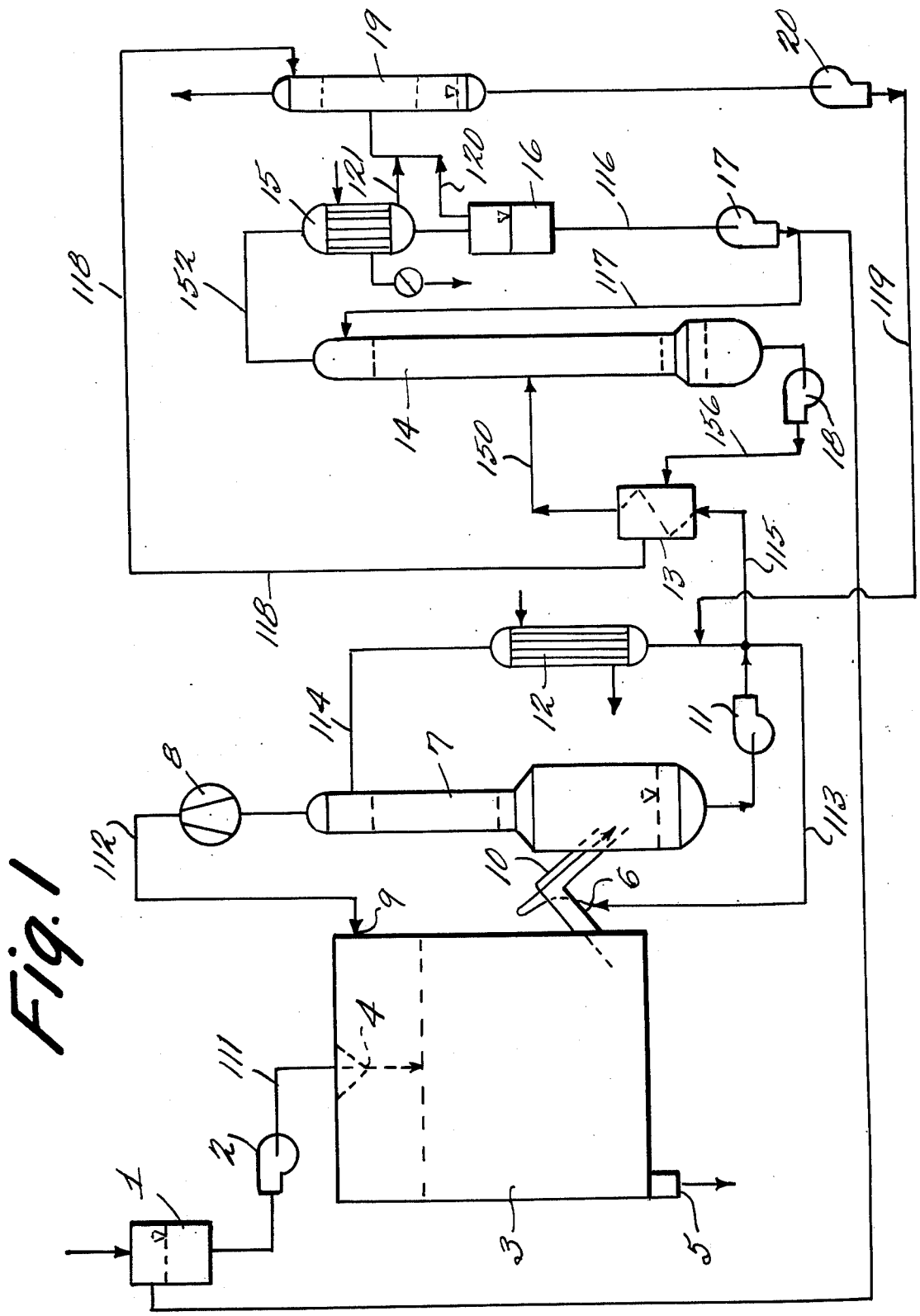

United States Patent [19]  [11] 4,038,276
Geiger et al. [45] July 26, 1977

[54] PROCESS FOR THE PRODUCTION OF FINELY DIVIDED SOLID CYANURIC CHLORIDE

[75] Inventors: Friedhelm Geiger, Erlensee; Werner Heimberger, Hanau; Theodor Lussling, Constance, all of Germany

[73] Assignee: Deutsche Gold- und Silber-Scheideanstalt vormals Roessler, Frankfurt, Germany

[21] Appl. No.: 716,353

[22] Filed: Aug. 20, 1976

[30] Foreign Application Priority Data

Aug. 23, 1975 Germany .............................. 2537673

[51] Int. Cl.² ........................................... C07D 251/28
[52] U.S. Cl. .................................................. 260/248 C
[58] Field of Search .................................... 260/248 C

[56] References Cited

U.S. PATENT DOCUMENTS

| 3,338,898 | 8/1967 | Foulletier | 260/248 C |
| 3,409,619 | 11/1968 | Kosel | 260/248 C |
| 3,925,377 | 12/1975 | Geiger et al. | 260/248 C |

*Primary Examiner*—John M. Ford
*Attorney, Agent, or Firm*—Cushman, Darby & Cushman

[57] ABSTRACT

Finely divided solid cyanuric chloride is produced by feeding a jet of liquid cyanuric chloride into a separatory container, cooling the liquid cyanuric chloride with recycling inert gases to such an extent that the cyanuric chloride is separated in crystalline form, washing the thereby warmed cyanuric chloride vapor or dust containing gases free of cyanuric chloride in countercurrent flow with an inert liquid that is a good solvent for cyanuric chloride in a washing column connected to the outlet side of the separatory column, thus simultaneously cooling the gases, and subsequently again returning the gases to the separatory container, while the temperature of the cyanuric chloride containing washing liquid which has increased in the washing process is again brought to the original temperature by leading it in the cycle over a heat exchanger and spraying the inside of the pipe connected to the separatory container and leading to the washing column constantly with the washing liquid while dividing a partial stream of the cyanuric chloride containing washing liquid in a distillation column into pure liquid cyanuric chloride which is recycled into the separatory column and into pure washing liquid which is recycled into the washing column.

10 Claims, 2 Drawing Figures

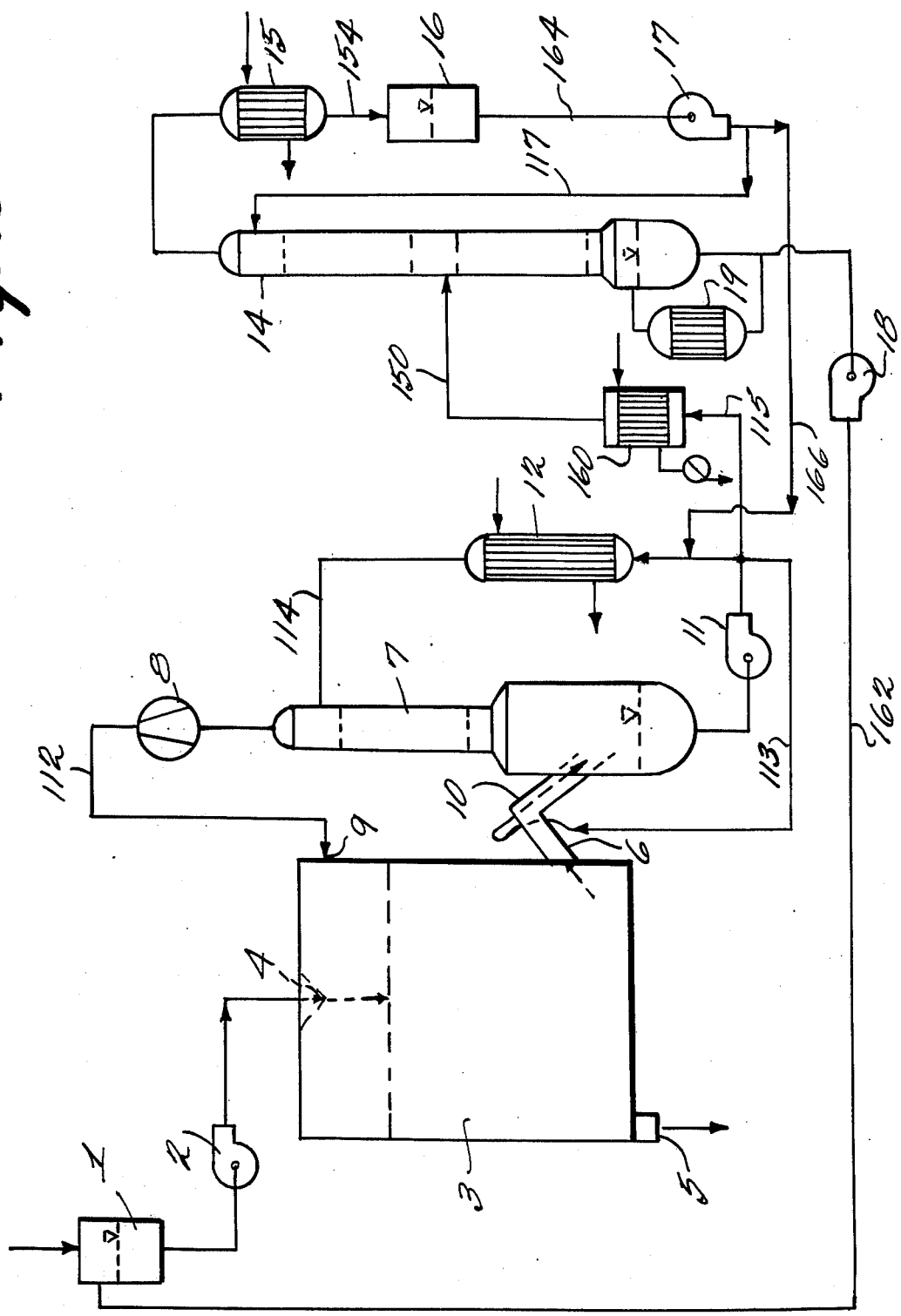

PROCESS FOR THE PRODUCTION OF FINELY DIVIDED SOLID CYANURIC CHLORIDE

It is known to separate vapor-form cyanuric chloride in solid form by desublimation in spaces cooled from the outside while avoiding the liquid phase. Hereby, there cannot be avoided that in addition to finely divided cyanuric chloride there is also formed coarse grained crystals which deposit on the installations and walls of the separator and after certain period of operation must be mechanically knocked off, see Kosel, German Pat. No. 1,266,308 and related Kosel, U.S. Pat. No. 3,409,619, e.g., column 1, lines 30 – 40.

Besides there are known processes for separating cyanuric chloride with the help of a cold, inert gas stream in which coarse aggregates are avoided, but in which the subsequently connected cyclone and the corresponding lines are clogged by solid deposits and in which besides the cyanuric chloride is discharged with the waste gas because of its high vapor pressure. For environmental reasons, the latter is impermissible, German Pat. No. 1,071,709.

These disadvantages are avoided if cyanuric chloride vapor is cooled using a special apparatus with the help of a cooling liquid which vaporizes in the cooling (Kosel, German Pat. No. 1,266,308 and U.S. Pat. No. 3,409,619). To be sure this method is not completely satisfactory because the separatory chamber in the lower part must be held at a temperature above the boiling point of the cooling liquid.

It has now been found that finely divided solid cyanuric chloride can be recovered while avoiding the above mentioned disadvantages by feeding liquid cyanuric chloride, e.g., in jet form, into a first (separatory) column, or container, cooling the liquid cyanuric chloride with inert gases to such an extent that the cyanuric chloride is separated in crystalline form, washing the thereby warmed cyanuric chloride vapor or dust containing gases free of cyanuric chloride in countercurrent flow with an inert liquid that is a good solvent for cyanuric chloride in a second (washing) column connected after the separatory column, thus simultaneously cooling the gases, and subsequently again returning the gases to the separatory container, while the temperature of the cyanuric chloride containing washing liquid which has increased in the washing process is again brought to the original temperature by leading it in the cycle over a heat exchanger and spraying the inside of the pipe connected to the separatory container and leading to the washing column constantly with the washing liquid while dividing a partial stream of the cyanuric chloride containing washing liquid in a third (distillation) column into pure liquid cyanuric chloride which is recycled into the separatory column and into pure washing liquid which is recycled into the washing column.

The lower the cooling gas temperature chosen, the smaller is the amount of circulating gas necessary for the cooling and crystallization of the liquid cyanuric chloride. Generally, there are employed gas temperatures of 0° – 100° C., preferably 20° – 60° C. As inert gas, there is particularly added air or nitrogen. However, other inert gases can be used, e.g., argon.

Contrary to the known desublimation of cyanuric chloride vapors in the step of solidification according to the process of the invention, only about ⅓ of the amount of heat evolved in the desublimation is removed since the heat of vaporization has already previously been removed in the liquefying of the cyanuric chloride in the system. Since the process of the invention operates with liquefied cyanuric chloride, therefore, there is added a cyanuric chloride which is free of chlorine and cyanogen chloride. The best procedure is according to the process of Geiger, German OS No. 2,332,636.5-4 or related Geiger, U.S. Pat. No. 3,925,377. The entire disclosure of the Geiger U.S. patent is hereby incorporated by reference and relied upon.

By this procedure, a separating off of the unreacted cyanogen chloride in the trimerization as well as any chlorine still present is unnecessary. This is a further substantial advantage of the process of the invention, since chlorine and cyanogen chloride, if they come in contact with the washing liquid used according to the invention can cause severe corrosion in the separatory column, in the pipes and pumps, as well as in the washing column.

Such corrosion can now be avoided since cyanuric chloride is completely free of these impurities.

If there is used for cooling the gases laden with cyanuric chloride vapor, a washing liquid whose boiling point is higher than that of cyanuric chloride then the cyanuric chloride dissolved in the washing liquid can be recovered through fractional distillation in a column whose condenser is held at temperatures above the melting point of cyanuric chloride and in a given case again can be returned to the feed. The solvent accumulating in the sump of this column is used in the cycling to again cool the inert gases.

In order to avoid the discharge of the waste gases of the distillation column in this type of recovery of washing liquid, a further washing column which is charged with the same solvent is connected downstream.

According to another embodiment, there can also be chosen a solvent whose boiling point is below the vaporization temperature of the cyanuric chloride, as for example, m-chlorotrifluorotoluene. In this, the solvent is then drawn off over the head of the column while pure liquid cyanuric chloride remains behind in the sump.

As washing liquid which serves both for cooling the recycled inert gases and also for dissolving out of the cyanuric chloride entrained because of its high vapor pressure, there are suited all inert liquids which dissolve cyanuric chloride, such as aliphatic or aromatic hydrocarbons, their halogenated derivatives, e.g., halogenated aliphatic hydrocarbons and halogenated aromatic, hydrocarbons, ketones or mixtures of these materials. Very suited are toluene, xylene, 1,2,4-trichlorobenzene, hexachlorobutadiene, dodecyl benzene, m-chlorotrifluorotoluene, hexafluoroxylene, trichlorotrifluoroethane, trifluoropentachloropropane, perfluorooctane or their mixtures. Other solvents include difluorotetrachloroethane, m-fluorotrifluorotoluene, m-bromotrifluorotoluene, m-hexafluoroxylene, 5-chlorohexafluoroxylene, 5-bromohexafluoroxylene, 5-fluorohexafluoroxylene, benzotrifluoride, 0- chlorotrifluorotoluene, p-chlorotrifluorotoluene, p-hexafluoroxylene, 0-hexafluoroxylene, 4-chloro-1,1,1-trifluoromethyl-3,3,3-trifluoromethyl benzene, 2-chloro-1,1,1-trifluoromethyl-3,3,3-trifluoromethyl benzene, methylene chloride, chloroform, acetone, methyl ethyl ketone, cyclohexanone. When halogenated hydrocarbons are used, the halogen usually is fluorine and/or chlorine. Especially preferred solvents are m-chlorotrifluorotoluene, hexafluoroxylene, dodecylbenzene and toluene.

When mixtures of solvents are used, preferably all of the solvents should either boil above cyanuric chloride or all should boil below cyanuric chloride.

To carry out the process of the invention, the pressure is not critical. The pressure range used, for example, can be 0.5 to 10 atmospheres (absolute pressure), preferably 1 to 5 atmospheres (absolute pressure).

FIG. 1 is a diagrammatic illustration of a process according to the invention using a solvent boiling above cyanuric chloride; and FIG. 2 is a diagrammatic illustration of an alternative process according to the invention using a washing liquid boiling below cyanuric chloride.

In the drawing, like numerals refer to like parts.

Unless otherwise indicated, all parts and percentages are by weight.

Referring more specifically to FIG. 1 of the drawings in which there is used a solvent whose boiling point is higher than the vaporization point of cyanuric chloride the liquid cyanuric chloride is led from the supply container 1 via pump 2 through conduit 111 to the separatory chamber 3 through the nozzle 4 and here atomized. On the separatory chamber 3, there is located outlet 5 for the solid cyanuric chloride and the withdrawal tube 6 through which the recycling gas is returned into the separatory column through the washing column 7 over the blower 8 and the line 112 at 9. A partial stream of solvent is led out of column 7 through pump 11 via line 113 at 10 into the discharge tube 7. A further partial stream is supplied to the washing column 7 via cooler 12 and line 114 against the gas stream.

Another part of the cyanuric chloride containing solvent is supplied via line 115 through the heat exchanger 13 and line 150 to the distillation column 14, from the top of which the cyanuric chloride goes via line 152 to the condenser 15 held at a temperature of above 150° C. and then the cyanuric chloride goes via line 154 to the receiver 16. The cyanuric chloride can either be recovered from the receiver as such, or as shown in FIG. 1, can be returned via line 116 over pump 17 into the supply container 1. A partial stream is diverted through line 117 as reflux into the distillation column 14. From the sump of column 14, the solvent via line 156 and pump 18 and the heat exchanger 13 passes through line 118 to the washing column 19 from whose sump it arrives back at the liquid recycling portion of the apparatus including the washing column 7 with the aid of pump 20 and via line 119. The condenser 15 and the distillation receiver 16 are deaerated by passing vapors via lines 120 and 121 into the washing column 19.

Unless otherwise indicated, all parts and percentages are by weight.

EXAMPLE 1 (Employing the Apparatus of FIG. 1)

(The boiling point of the washing medium is above the boiling point of cyanuric chloride).

There were sprayed into the separatory chamber 3 from the supply container 1 with the help of pump 2 via the line 111 and the nozzle 4 hourly 2.5 kg of liquid cyanuric chloride having a temperature of 150° C. Simultaneously, there were introduced 36 Nm³/h (36 normal cubic meters per hour) of nitrogen with a temperature of 20° C. at the point indicated by numeral 9. The cyanuric chloride at 50° C. and containing nitrogen leaving the separatory chamber 3 via withdrawal tube 6 whose wall 10 was sprayed with dodecyl benzene is cooled in the washing column by counter current flow of 100 kg/h of dodecyl benzene and simultaneously washed free of cyanuric chloride and returned again into the separatory chamber 3 at 9 via blower 8 and line 112. The dodecyl benzene was cooled with the help of heat exchanger 12 to such an extent that the cycling gas at 20° C. can be returned via blower 8 into the separator chamber 3.

From the solvent cycle 7, 11, 12 and 114 hourly there were pumped 10.3 kg of a 3% solution of cyanuric chloride in dodecyl benzene with the help of the pump 11 via line 115 and the heat exchanger 13 into the distillation column 14 where there took place a distillative separation into pure liquid cyanuric chloride and pure dodecyl benzene. The dodecyl benzene collecting in the sump was led to the top of waste gas washing column 19 with the help of the pump 18 via the heat exchanger 13 and the line 118 and from here went back to the head of washing column 7 via pump 20, the line 119, the condenser 12 and the line 114.

The cyanuric chloride collected at the top (head) of the distillation column 14 was cooled in the condenser 15 to 150° C. and recycled in liquid form via the receiver 16, pump 17 and line 116 into the liquid cyanuric chloride supply container 1.

In order to quantitatively concentrate the dodecyl benzene in the sump of the column 14, a partial stream of the condensed cyanuric chloride from the receiver 16 was branched as reflux into the top of distillation column 14 by means of pump 17 and via line 117. In order to avoid the cyanuric chloride containing waste gases being carried out into the atmosphere, the condenser 15 via line 121 and the receiver 16 via line 120 are deaerated into the washing column operated with dodecyl benzene.

Solid cyanuric chloride with a particle size distribution between 10 and 80μ was collected at the bottom of the separatory chamber 3 and was removed through outlet 5.

EXAMPLE 2 (FIG. 2)

(The boiling point of the washing medium lies below the boiling point of the cyanuric chloride).

There were sprayed into the separatory chamber hourly 2.5 kg of liquid cyanuric chloride at a temperature of 150° C. from supply container 1 with the help of pump 2 via line 111 and nozzle 4. Simultaneously there were led in 36 Nm³l/h of nitrogen at a temperature of 20° C. at the point indicated by 9.

The cyanuric chloride at 50° C. and containing nitrogen leaving the separatory chamber 3 goes via withdrawal tube 6 whose wall 10 is sprayed with m-chloobenzotrifluoride from line 113 into washing column 7 and the nitrogen containing cyanuric chloride was cooled by countercurrent flow of 100 kg/h of m-chlorobenzotrifluoride (m-chlorotrifluorotoluene), simultaneously washed free of cyanuric chloride and returned again into the separatory chamber 3 at 9 via blower 8 and line 12. The m-chlorobenzotrifluoride was cooled with the help of heat exchanger 12 to such an extent that the cycling gas at 20° C. can be returned into the separatory chamber 3. From the solvent cycle 7, 11, 12 and 114, hourly there were pumped 10.3 kg of a 3% solution of cyanuric chloride in m-chlorobenzotrifluoride with the help of pump 11 via line 115 and the heater 160 into the distillation column 14 where there took place a distillative separation into pure liquid cyanuric chloride and pure m-chlorobenzotrifluoride.

The liquid cyanuric chloride collecting in the sump of column 14 was pumped with the help of pump 18 via line 162 into supply container 1 while the cyanuric chloride free m-chlorobenzotrifluoride drawn off at the top of column 14 was recycled to the top of washing column 7 via the line 152, condenser 15, line 154, receiver 16 with the help of pump 17, via line 164 and 166 to the heat exchanger 12 and finally via line 114.

In order to quantitatively concentrate the cyanuric chloride in the sump of column 14 a partial stream of the condensed solvent was branched as reflux into the top of distillation column 14 by means of pump 17 and via line 117.

Solid cyanuric chloride with a particle size distribution between 10 and 80μ was collected at the bottom of the separatory chamber 3 and was removed through outlet 5.

There could not be detected any loss of cyanuric chloride.

The process can comprise, consist essentially of or consist of the steps set forth using the indicated materials.

What is claimed is:

1. A process of producing finely divided solid cyanuric chloride comprising feeding liquid cyanuric chloride into a separatory container, cooling the liquid cyanuric chloride with recycling inert gas to such an extent that the cyanuric chloride separates in crystalline form, passing and thereby warmed inert gas now containing cyanuric chloride vapor from said separatory container through a conduit into a washing column, washing the cyanuric chloride laden gas in said washing column by countercurrent flow with an inert liquid that is a good solvent for cyanuric chloride, which liquid solvent has a temperature below that of the warmed gas, to remove cyanuric chloride from said gas while simultaneously cooling the gas, subsequently returning the thus cooled and purified gas to the separatory container, cooling to the original temperature the washing liquid containing cyanuric chloride, which liquid had increased in temperature in the washing process and spraying the inside of the conduit connecting the separatory container and washing column constantly with the cooled washing liquid, dividing a partial stream of the cyanuric chloride containing washing liquid in a distillation column into a pure liquid cyanuric chloride fraction, and a pure washing liquid, recycling the pure liquid cyanuric chloride into the separatory column and recycling the pure washing liquid into the washing column.

2. A process according to claim 1 wherein the washing liquid boils above cyanuric chloride and is removed from the lower part of the distillation column while the cyanuric chloride is removed from the upper part of the distillation column.

3. A process according to claim 1 wherein the washing liquid boils below cyanuric chloride and is removed from the upper part of the distillation column while the cyanuric chloride is removed from the bottom part of the distillation column.

4. A process according to claim 1 wherein the inert gas is nitrogen.

5. A process according to claim 1 wherein the temperature of the inert gas used to cool the liquid cyanuric chloride is 0° to 100° C.

6. A process according to claim 5 wherein the temperature of the inert gas is 20° to 60° C.

7. A process according to claim 5 wherein the washing liquid for the cyanuric chloride laden inert gas is an aliphatic hydrocarbon, an aromatic hydrocarbon, a halogenated aliphatic hydrocarbon or a halogenated aromatic hydrocarbon or a mixture thereof.

8. A process according to claim 1 wherein the washing liquid for the cyanuric chloride laden inert gas is an aliphatic hydrocarbon, an aromatic hydrocarbon, a halogenated aliphatic hydrocarbon or a halogenated aromatic hydrocarbon or a mixture thereof.

9. A process according to claim 8 wherein the washing liquid is toluene, xylene, 1,2,4-trichlorobenzene, hexachlorobutadiene, dodecyl benzene, m-chlorotrifluorotoluene, hexafluoroxylene, trichlorotrifluoroethane, trifluoropentachloropropane, perfluorooctane or mixtures thereof.

10. A process according to claim 9 wherein the washing liquid is m-chlorotrifluorotoluene, hexafluoroxylene, dodecyl benzene or toluene.

* * * * *